US011523939B2

(12) United States Patent
Tai et al.

(10) Patent No.: US 11,523,939 B2
(45) Date of Patent: Dec. 13, 2022

(54) MINIATURE FIXED AND ADJUSTABLE FLOW RESTRICTOR FOR THE BODY

(71) Applicants: California Institute of Technology, Pasadena, CA (US); University of Southern California, Los Angeles, CA (US)

(72) Inventors: Yu-Chong Tai, Pasadena, CA (US); Aubrey M. Shapero, Pasadena, CA (US); Nicholas E. Scianmarello, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 493 days.

(21) Appl. No.: 16/418,899

(22) Filed: May 21, 2019

(65) Prior Publication Data

US 2019/0358082 A1 Nov. 28, 2019

Related U.S. Application Data

(60) Provisional application No. 62/674,737, filed on May 22, 2018.

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61M 31/002* (2013.01);
(Continued)

(58) Field of Classification Search
CPC ............ A61F 9/0017; A61F 2250/0068; A61F 9/00781; A61F 2009/00872;
(Continued)

(56) References Cited

U.S. PATENT DOCUMENTS 1,543,506 A    6/1925   Miller
3,515,095 A    6/1970   Baranow et al.
(Continued)

FOREIGN PATENT DOCUMENTS

CN    101616640     12/2009
CN    102316833 A    1/2012
(Continued)

OTHER PUBLICATIONS

EP16858334.2 , "Extended European Search Report", dated Jul. 23, 2019, 8 pages.
(Continued)

*Primary Examiner* — Quang D Thanh
*Assistant Examiner* — Brandon W. Levy
(74) *Attorney, Agent, or Firm* — Kilpatrick Townsend & Stockton LLP

(57) ABSTRACT

A microfluidic flow restrictor that uses micron-sized beads to impede flow is described. The flow rate can be adjusted by adding or removing the beads using injection needles through self-sealing ports, one injection needle injecting or aspirating beads and another injection needle pushing or pulling fluid from outside of a bead trap within the flow restrictor. In alternative embodiments, the beads or other filler material can be trapped in a manifold bead trap such that they block a subset of fluid channels of the flow restrictor, allowing fluid to flow freely through the rest of the fluid channels. The flow restrictor can be integrated with a contact lens or implantable medical device for use in dispensing liquid therapeutic agents at flow rates of microliters (Continued)

per minute or moving body fluids at a controlled rate from one part of the body to another.

20 Claims, 7 Drawing Sheets

(51) Int. Cl.
  *A61M 31/00* (2006.01)
  *G02C 7/04* (2006.01)
(52) U.S. Cl.
  CPC . *A61F 2250/0068* (2013.01); *B01L 2400/082* (2013.01); *G02C 7/049* (2013.01)
(58) Field of Classification Search
  CPC .. A61F 2009/00865; A61F 2/16; A61F 2/142; A61F 2009/00863; A61F 2009/0087; A61K 9/0051; A61M 31/002; A61M 2210/0612; A61M 5/16881; A61M 2205/04; B01L 2400/082; B01L 2200/0668; B01L 2200/082; B01L 2300/0861; B01L 2200/027; B01L 2300/0877; G02C 7/049; G02C 7/04; B01J 2219/005; B01J 2219/00459; A61B 5/6821
  See application file for complete search history.

(56) References Cited

U.S. PATENT DOCUMENTS

| | | | |
|---|---|---|---|
| 4,572,846 A | 2/1986 | Foss et al. | |
| 4,942,018 A | 7/1990 | Munk | |
| 5,393,103 A | 2/1995 | Cretzler | |
| 5,472,436 A | 12/1995 | Fremstad | |
| 5,534,068 A | 7/1996 | Beach et al. | |
| 8,133,512 B2 | 3/2012 | Kunzler et al. | |
| 8,372,046 B2 | 2/2013 | Meng et al. | |
| 8,404,265 B2 | 3/2013 | Chauhan et al. | |
| 8,404,271 B2 | 3/2013 | Byrne et al. | |
| 8,623,400 B2 | 1/2014 | Liu et al. | |
| 8,663,194 B2 | 3/2014 | Ambati et al. | |
| 9,086,580 B2 | 7/2015 | Grant et al. | |
| 9,091,865 B2 | 7/2015 | Hofmann et al. | |
| 9,421,126 B2 | 8/2016 | Alster et al. | |
| 9,655,774 B2 | 5/2017 | Tai et al. | |
| 9,763,825 B2 | 9/2017 | Tai et al. | |
| 9,782,346 B2 | 10/2017 | Venkatraman et al. | |
| 9,937,073 B2 | 4/2018 | de Juan, Jr. et al. | |
| 10,031,348 B2 | 7/2018 | Tai et al. | |
| 10,092,387 B2 | 10/2018 | Tai et al. | |
| 10,768,444 B2 | 9/2020 | Tai et al. | |
| 11,051,977 B2 | 7/2021 | Tai et al. | |
| 11,077,462 B2 | 8/2021 | Tai et al. | |
| 2008/0023324 A1* | 1/2008 | Ban | B01L 3/502753 |
| | | | 204/400 |
| 2008/0035875 A1 | 2/2008 | Tai et al. | |
| 2008/0169427 A1 | 7/2008 | Hatem et al. | |
| 2008/0231799 A1 | 9/2008 | Iuliano | |
| 2008/0286338 A1 | 11/2008 | Rosenthal et al. | |
| 2010/0114309 A1 | 5/2010 | de Juan, Jr. et al. | |
| 2010/0217209 A1 | 8/2010 | Meng et al. | |
| 2011/0116035 A1 | 5/2011 | Fritsch et al. | |
| 2011/0184358 A1 | 7/2011 | Weiner et al. | |
| 2011/0282328 A1 | 11/2011 | Ambati et al. | |
| 2012/0022473 A1 | 1/2012 | Shikamura et al. | |
| 2012/0115189 A1 | 5/2012 | Jovanovich et al. | |
| 2012/0268712 A1 | 10/2012 | Egan et al. | |
| 2012/0302972 A1 | 11/2012 | Higuchi | |
| 2014/0005514 A1 | 1/2014 | Pugh et al. | |
| 2014/0193045 A1 | 7/2014 | Otis et al. | |
| 2014/0235457 A1 | 8/2014 | Esfandyarpour et al. | |
| 2014/0236066 A1* | 8/2014 | Horvath | A61L 31/08 |
| | | | 604/9 |
| 2015/0111023 A1 | 4/2015 | Tai et al. | |
| 2015/0293031 A1 | 10/2015 | Fisk | |
| 2016/0109726 A1 | 4/2016 | Tai et al. | |
| 2017/0001195 A1* | 1/2017 | Unger | B01L 9/527 |
| 2017/0113246 A1 | 4/2017 | Tai et al. | |
| 2017/0136463 A1 | 5/2017 | Tai et al. | |
| 2018/0333298 A1 | 11/2018 | Tai et al. | |

FOREIGN PATENT DOCUMENTS

| | | | |
|---|---|---|---|
| CN | 105435338 A | 3/2016 | |
| WO | WO-2007106557 A2 * | 9/2007 | ........ A61M 5/16881 |
| WO | 2008083118 A1 | 7/2008 | |
| WO | 2010041230 A2 | 4/2010 | |
| WO | 2016061125 | 4/2016 | |
| WO | 2017/070528 | 4/2017 | |

OTHER PUBLICATIONS

PCT/US2019/033369, "International Search Report and Written Opinion", dated Sep. 17, 2019, 11 pages.
PCT/US2019/036498, "International Search Report and Written Opinion", dated Oct. 31, 2019, 12 pages.
PCT/US2019/036498, "Invitation to Pay Additional Fees and, Where Applicable, Protest Fee", dated Aug. 19, 2019, 2 pages.
PCT/US2019/033369, "International Preliminary Report on Patentability", dated Dec. 3, 2020, 8 pages.
PCT/US2019/036498, "International Preliminary Report on Patentability", dated Dec. 24, 2020, 9 pages.
Arai et al., "Long-Term Electroencephalogram Measurement Using Polymer-Based Dry Microneedle Electrode", IEEE, Transducers 2015, Anchorage, Alaska, Jun. 21-25, 2015, pp. 81-84.
Chang et al., "High Yield Packaging for High-Density Multi-Channel Chip Integration of Flexible Parylene Substrate", IEEE, MEMS 2012, Paris, France, Jan. 29-Feb. 2, 2012, pp. 353-356.
Chang et al., "Packaging Study for a 512-Channel Intraocular Epiretinal Implant", IEEE, MEMS 2013, Taipei, Taiwan, Jan. 20-24, 2013, pp. 1045-1048.
Kang et al., "Effects of Deposition Temperature on Parylene-C Properties", IEEE, MEMS 2013, Taipei, Taiwan, Jan. 20-24, 2013, pp. 389-392.
Kramer et al., "Polymerization of Para-Xylylene Derivatives (Parylene Polymerization). I. Deposition Kinetics for Parylene N and Parylene C", Journal of Polymer Science, Polymer Chemistry Edition, vol. 22, 1984, pp. 475-491.
Metzen et al., "Diffusion Limited Tapered Coating with Parylene C", IFMBE Proceedings 25/IX, 2009, pp. 96-97.
Metzen et al., "Diffusion-Limited Deposition of Parylene C", Journal of Microelectromechanical Systems, vol. 20, No. 1, Feb. 2011, pp. 712-724.
Ramachandran et al., "A Study of Parylene C Polymer Deposition Inside Microscale Gaps", IEEE Transactions on Advanced Packaging, vol. 30, No. 4, Nov. 2007, pp. 712-724.
Sawano et al., "Sealing Method of PDMS as Elastic Material for MEMS", IEEE, MEMS 2008, Tucson, Arizona, Jan. 13-17, 2008, pp. 419-422.
Senkevich et al., "Thermomechanical Properties of Parylene X, A Room-Temperature Chemical Vapor Depositable Crosslinkable Polymer", Chemical Vapor Deposition, vol. 13, 2007, pp. 55-59.
Wang et al., "Reliable Deposition of Ultra-Thin Parylene", IEEE 2016, MEMS 2016, Shanghai,China, Jan. 24-28, 2016, pp. 462-464.
"Compliance Problems with Glaucoma Eye Drops," OpthalmologyWeb, Available Online at: https://www.ophthalmologyweb.com/Featured-Articles/19875-Compliance-Problems-with-Glaucoma-Eye-Drops/, Aug. 23, 2010, 3 pages.
"How to Succeed at Eye Drop Treatment: It's All in Your Hands," Glaucoma Center of Excellence, Available online at: https://www.hopkinsmedicine.org/wilmer/services/glaucoma/book/chapter_how_to_succeed_with_drops.html, Accessed from Internet on Jun. 14, 2019, 7 pages.
"Improving Compliance Through Access to Eye Drop Medication," Available online at: https://www.cameron-graham.co.uk/pages/pharmacists.php, Accessed from Internet on Jun. 14, 2019, 2 pages.

(56) References Cited

OTHER PUBLICATIONS

"The Role of the Pharmacist in Improving Glaucoma Compliance," Ear and Eye Care, NI Pharmacy in Focus, Available online at: https://www.cameron-graham.co.uk/pages/pharmacists.php, Aug. 2005, 1 page.
PCT/US2019/033368, "Invitation to Pay Additional Fees and, Where Applicable, Protest Fee," dated Jul. 3, 2019, 2 pages.
Robin, "Beyond Compliance: Getting the Drops in," Review of Ophthalmology, Available online at: https://reviewofophthalmology.com/article/beyond-compliance-getting-the-drops-in, Feb. 18, 2010, 5 pages.
EP19820418.2, "Extended European Search Report", dated Feb. 15, 2022, 9 pages.
PCT/US2015/055368, "International Preliminary Report on Patentability", dated Apr. 27, 2017, 10 pages.
PCT/US2015/055368, "International Search Report and Written Opinion", dated Feb. 16, 2016, 12 pages.
PCT/US2016/058200, "International Preliminary Report on Patentability", dated May 3, 2018, 12 pages.
PCT/US2016/058200, "International Search Report and Written Opinion", dated Jan. 10, 2017, 13 pages.

\* cited by examiner

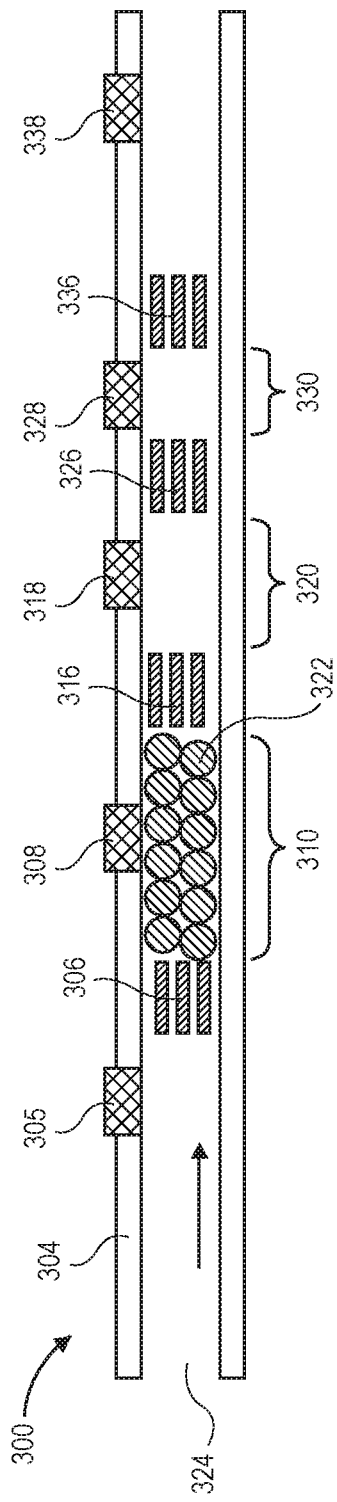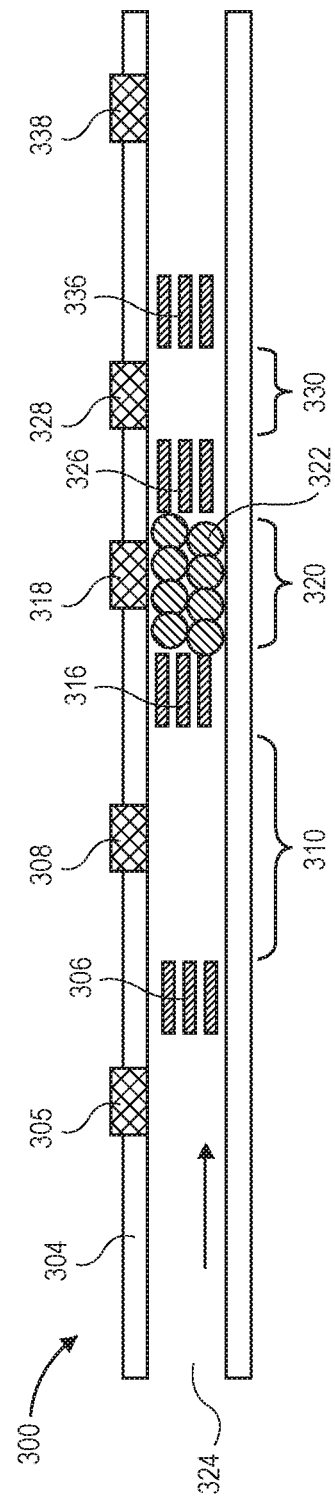

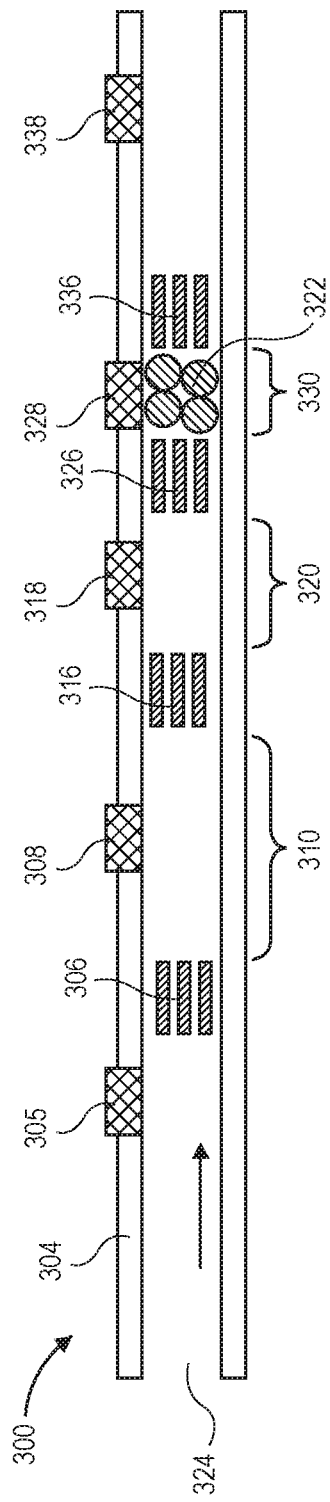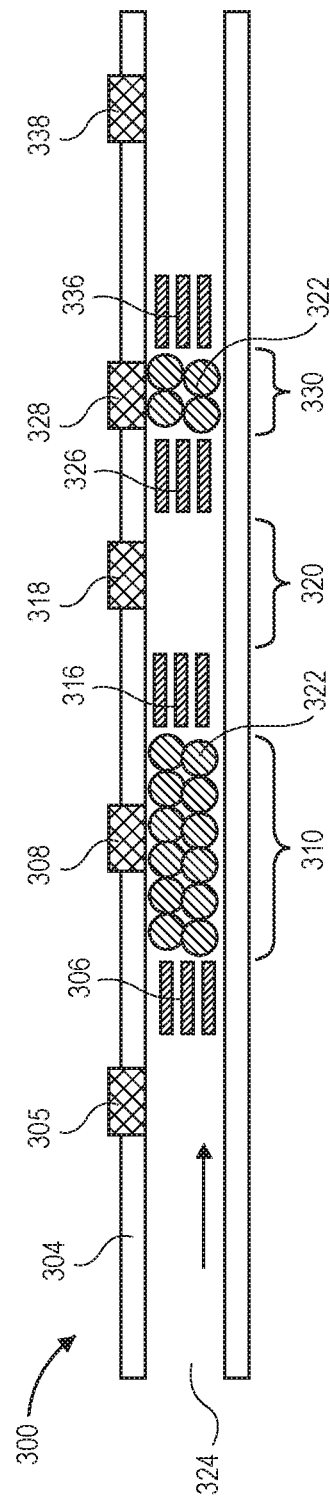

MINIATURE FIXED AND ADJUSTABLE FLOW RESTRICTOR FOR THE BODY

CROSS-REFERENCES TO RELATED APPLICATIONS

This application claims the benefit of U.S. Provisional Application No. 62/674,737, filed May 22, 2018, the contents of which are hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

The present application generally relates to implanted devices specially adapted for bringing pharmaceutical products into the body. Specifically, it relates to a micro-miniature flow restrictor to dispense liquid therapeutics over long timeframes from a contact lens or other medical device.

2. Description of Related Art

Treatment of eye-related pathologies sometimes requires frequent visits to an eye doctor or other physician. Some treatments require compositions in liquid form to be applied within or on the eye. Liquid drugs that are applied to the eye get diluted by an almost constant inflow of fluid from tear ducts. Evaporation to the atmosphere and wicking to other areas of the eye also disturb whatever dose of liquid therapeutics are applied. A patient may have to schedule repeated visits to a doctor to apply drugs repeatedly in order to keep the drug compound at the proper concentration. Even if application of the drug does not require visits to the doctor, the patient must remember to apply the drug repeatedly.

The most common treatment for various eye conditions is through topical application of ophthalmic solutions or eye drops. This method of fluid delivery to the eye accounts for 90% of all the ophthalmic medications. This mode of delivery, however, is inefficient, with sometimes less than 10% absorption in the eye of the medicine from the eye drops.

Keeping a constant concentration of a drug is a problem in almost any part of a living body. Animal bodies move, and they have adapted to flush foreign matter, including liquid drugs, from their internal systems. Their immune systems employ active defenses that vigorously remove non-natural impurities. Keeping a constant dose of a drug near the spine, heart, or other internal organs must fight against this constant variation and dilution. Keeping a constant dose on the skin must overcome these issues as well.

It would be beneficial to be able to deliver ophthalmic fluids and medications more precisely and effectively. Delivering a liquid drug at a constant rate over time from a reservoir is one solution. If the reservoir of drug is large enough, and the amount delivered is metered at small enough amounts, then many of the above-referenced problems could be overcome. Measured, precise liquid drug delivery over days and months to a patient going about his or her daily live has been a long sought after goal.

Yet controlling drug delivery at small scales, in the confined and harsh environment of a body, has proved elusive. Small tubes tend to foul, batteries discharge, and common solutions for flow control not designed for miniature biological applications fail. For example, pumps and flow restrictors meant for the macro world of buildings or hospital machinery do not work well when miniaturized.

Existing medical equipment actuation and metering systems would be difficult, if not impossible, to miniaturize into a scale that is implantable or that can fit into a contact lens. Most actuation and metering systems require a variety of power sources, electrical systems, and other hardware to function properly. Further, their function often depends on materials that are not biocompatible, for example rare earth metal magnets for motors and solenoids. Such systems would not be cost effective for disposable short term applications. Static friction, or "stiction," of mechanical elements is also different at smaller scales than it is on a macroscopic scale.

There is a need in the art for improved devices and methods for dispensing liquid drugs on or within a body, or more fundamentally, controlling the flow rate of fluid from a reservoir or one part of the body to another part of the body.

BRIEF SUMMARY

Generally described is a microfluidic flow restrictor that uses a plethora of micron-sized spheres, or "beads," to inhibit fluid flow. The small scale of the beads allows control of a liquid down to extremely small volumes and flow rates, e.g., flow rates measured in microliters per minute ($\mu$L/min). The constant, spherical geometry of the beads allows predictably spaced interstitial passages. Micron-sized, spherical beads are readily manufacturable and commercially available. On the flow restrictor are multiple ports for adding or removing beads from the flow restrictor by way of injection needles or otherwise, where one needle may be injecting or removing beads while another needle is sucking or pushing fluid to help move the beads. Adding and removing beads can calibrate the device to a standard set point or to an optimal value for a particular patient.

Alternative aspects include a microfabricated set of parallel fluid channels in bulk material with a common input or output manifold. The manifold holds beads or other material that restricts fluid from flowing through a subset of the channels. Ports are included to add or remove beads from the manifold. Adding more beads blocks off more channels; removing beads frees them up.

Some embodiments of the present invention are related to a microfluidic flow restrictor apparatus, including a fluid channel having walls, a first bead stop within the fluid channel, a second bead stop within the fluid channel, the first and second bead stops forming a bead trap within the fluid channel, a fill port extending from an outside of the walls to an interior of the bead trap, and a downstream needle port extending from an outside of the walls to a portion of the fluid channel downstream of the bead trap.

The flow restrictor can include a non-pierceable needle stop on or within a wall opposite at least one of the fill port and the downstream port. The non-pierceable needle stop may comprise glass.

The flow restrictor can include a plurality of chemically inert spherical beads within the bead trap. The spherical beads can each have a diameter between 10 $\mu$m and 100 $\mu$m. The flow restrictor can include a liquid flowing within the fluid channel, the beads within the bead trap causing a pressure drop of less than 103 kilopascals (15 pounds per square inch). The spherical beads can be porous.

The bead trap may be called a first bead trap and the fill port called a first fill port, with the flow restrictor further including a third bead stop within the fluid channel, the second and third bead stops forming a second bead trap within the fluid channel, and a second fill port extending from the outside of the walls to an interior of the second bead trap, whereby both or either first or second bead trap may be selectively filled with beads in order to modify a flow resistance of the microfluidic flow restrictor apparatus. The first bead trap can have a different length from the second bead trap. A non-pierceable needle stop can be or within a wall opposite the second fill port.

At least one of the fill port or the downstream port can be dyed or otherwise colored so as to be visually contrasted from other portions of the walls. At least one of the fill port or the downstream port can be thicker than the walls of the fluid channel. The fill port and downstream port can each comprise silicone rubber and have a thickness greater than 160 µm so as to make them self-sealing to a 21-gauge injection needle. The fill port and downstream port can each comprise parylene C and have a thickness greater than 5 µm so as to make them self-sealing to a 21-gauge injection needle.

The bead trap can form a U shape such that the fill port is proximate the downstream port. The bead trap can have a length of less than 1 centimeter. The fluid channel, first and second bead stops, and fill port can have squared off corners resulting from photolithography and etching.

Some embodiments are related to a contact lens including the microfluidic flow restrictor apparatus, a reservoir connected with an inlet of the flow restrictor apparatus, and an eye-contacting surface connected with an outlet from the microfluidic flow restrictor apparatus.

Some embodiments are related to a method of adjusting a microfluidic flow restrictor, the method including measuring a fluid flow rate through a microfluidic flow restrictor having a bead trap with a fill port, piercing the fill port with an injection needle, injecting chemically inert spherical beads into, or aspirating chemically inert spherical beads out of, a bead trap in the microfluidic flow restrictor using the injection needle, the chemically inert spherical beads having a diameter between 10 µm and 100 µm, thereby adjusting a fluidic resistance of the microfluidic flow restrictor, and re-measuring the fluid flow rate after the injecting.

The injection needle may be called a first injection needle, and the method can further include piercing a downstream port of the microfluidic flow restrictor with a second injection needle, pulling or pushing fluid with the second injection needle contemporaneously with the injecting or aspirating of the first injection needle in order to assist movement of the spherical beads. The method can further include vibrating, using an ultrasound transducer, a wall of the microfluidic flow restrictor in order to dislodge spherical beads.

Some embodiments are related to a microfluidic flow restrictor apparatus including multiple parallel fluid channels, each fluid channel having a bead stop, a manifold connected with and running perpendicular to the fluid channels, a first bead stop within the manifold, the first bead stop of the manifold and bead stops of the multiple parallel fluid channels forming a single bead trap within the manifold, a self-sealing fill port extending from an outside into an interior of the bead trap, and a self-sealing downstream port extending from the outside to a portion of the manifold not within the bead trap.

The flow restrictor can further include a non-pierceable needle stop on or within a wall opposite at least one of the fill port or the downstream port. It can include a plurality of chemically inert spherical beads within the manifold bead trap and against a bead stop of a first fluid channel of the multiple fluid channels and not against a bead stop of a second fluid channel of the multiple fluid channels, thereby blocking the first fluid channel with respect to the second fluid channel. At least one of the port fill port and the downstream port can be dyed so as to be visually contrasted from other portions of the flow restrictor apparatus. At least one of the fill port and the downstream port can be thicker than walls of the manifold.

Some embodiments include a contact lens including the microfluidic flow restrictor apparatus, a reservoir connected with an inlet of the flow restrictor apparatus, and an eye-contacting surface connected with an outlet from the microfluidic flow restrictor apparatus.

Some embodiments are related to a microfluidic flow restrictor apparatus including a fluid channel having walls, a first bead stop within the fluid channel, a second bead stop within the fluid channel, the first and second bead stops forming a bead trap within the fluid channel, and a plurality of chemically inert spherical beads within the bead trap, wherein the spherical beads have a diameter between 10 µm and 100 µm.

A further understanding of the nature and the advantages of the embodiments disclosed and suggested herein may be realized by reference to the remaining portions of the specification and the attached drawings.

BRIEF DESCRIPTION OF THE DRAWINGS

FIG. 3A illustrates a flow restrictor having beads in an upstream bead trap in accordance with an embodiment.

FIG. 3B illustrates the flow restrictor of FIG. 3A having beads in a central bead trap.

FIG. 3C illustrates the flow restrictor of FIG. 3A having beads in a downstream bead trap.

FIG. 3D illustrates the flow restrictor of FIG. 3A having beads in multiple bead traps.

DETAILED DESCRIPTION

Figure 1:
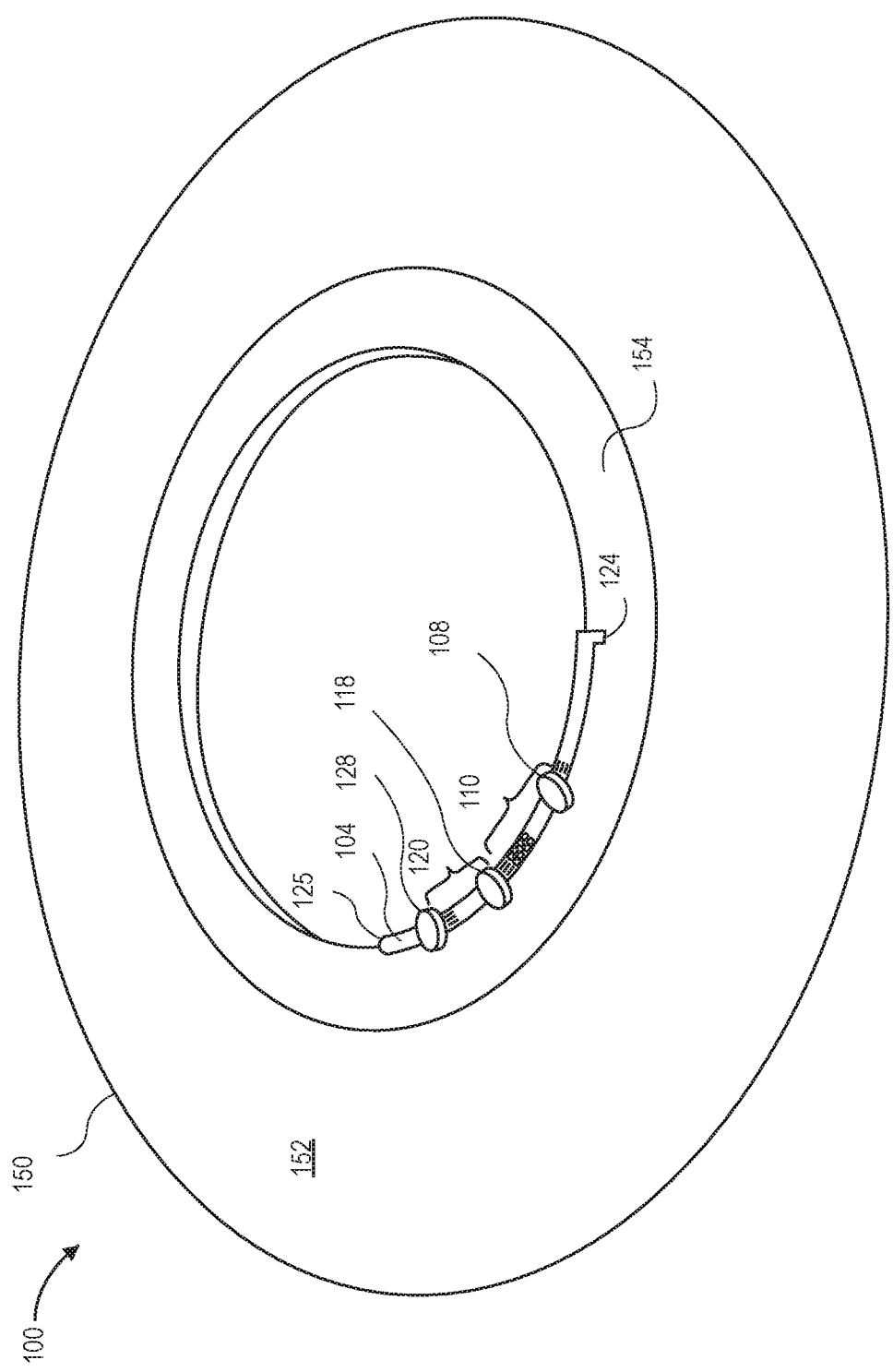
FIG. 1 illustrates a contact lens in accordance with an embodiment.

A miniature device that allows the flow of fluid at a variable rate, inside or on or in contact with living tissue, is described. Possible applications include the drainage of intraocular fluid at a rate that is fixed or may be adjusted after implantation for the treatment of glaucoma, the drainage of cerebral spinal fluid at an adjustable rate after implantation for the treatment of hydrocephalus, fluidic drug release, and the restriction of flow gas, such as air.

The flow restrictor is a channel with two openings. The inlet resides inside an organ or mated to a reservoir chamber, and an outlet at another location, and two or more self-sealing ports can be along the channel. A self-sealing port may be made of soft materials, such as a silicone septum that can be punctured by a needle but does not leak after the needle is removed due to compression. For example, for a glaucoma drainage device, the inlet may reside inside the eye, and the outlet may reside outside the sclera, where the ports are accessible underneath the conjunctiva.

In one version, there is a bead trap between the two ports, where the port closer to the inlet is the upstream port, and the port closer to the outlet is the downstream port. Biocompatible beads, such as glass beads, are inserted into the channel through the upstream port through a needle, and meanwhile suction can be drawn through the downstream port by another needle. The size and number of beads can influence the flow resistance.

Flow resistance is defined as the total pressure drop from one point in the channel to another, per unit of flow (volume/time), ignoring any hydrostatic pressure difference due to height difference, or as otherwise defined in the art.

Bead porosity is another parameter which can influence the flow resistance. In addition to beads, other removable media may be used to restrict flow to the desired amount, such as porous gel, hydrogel, or wax. These may be used to select the flow resistance of a single channel or to open or close various parallel channels to digitally select the flow resistance. Depending on the material of the flow inhibitor, an appropriate stop may be used to confine the inhibiting material, such as a filter or confined gap, or narrowing of the channel. In addition to the materials listed as removable materials, a fixed flow resistance can be selected out of these materials or other porous biocompatible materials, such as sol-gel or fibrous material like poly(ethylene), PET (polyethylene terephthalate), nylon, polytetrafluoroethylene (PTFE) or other TEFLON® fiber, or cellulose or other fibrous membranes commonly used for dialysis filtering, etc.

The flow-inhibiting material insertion process is reversible such that medical measurements post implantation can be considered for appropriate modifications of the fluid restriction. For example, excessive intraocular pressure measurement may suggest the reduction of the fluid restriction. Fluid may be injected into the downstream port while suction is applied to the upstream port to remove all of the material, such as beads. Afterwards, a different number of beads with possible different bead diameters or porosity may be inserted according to any updated information. In this manner, the flow resistance does not have to be guessed a priori, as it can be increased or decreased after implantation as often as necessary, or according to time-dependent behavior.

Filters or bead traps can ensure that material or beads do not leak outside of the desired region inside the flow restrictor. If any biological fouling occurs on the beads over time such that the flow resistance changes, the beads or gel, etc. can be removed and replaced. These filters can be designed to contain the inhibiting material, but not significantly influence the flow restriction.

A glass slide or other rigid material may be present below the needle insertion points to prevent puncturing through the bottom of the channel. The channel itself may be made of biocompatible materials such as silicone, parylene (poly(p-xylylene)), glass, acrylic such as PMMA (poly(methyl methacrylate)), or titanium or other metals or alloys, or other materials like silicon, or a combination thereof. The self-sealing port may be made out more biocompatible flexible materials such as silicone, hydrogel and PVA (polyvinyl alcohol), etc.

As opposed to trying to limit flow using the size of tubes, embodiments have channels that are relatively large (50 micron to 1 mm in diameter), yet can achieve comparable flow resistance through the use of flow inhibiting material. In this way, one can avoid problems that arise when tubes are too small such as clogging. Especially at small dimensions, the flow resistance is highly sensitive to the inner diameter (inverse radius^4) of a tube, so this approach is qualitatively different. Beads between 0.1 to 1,000 microns in diameter can be used. The pore size of the filter should capture the beads, so pore or filter size of the same range (0.1 to 1,000 microns) is advised. The overall external dimensions can be as small as 1 mm to 100 cm, depending on the application.

FIG. 1 illustrates a ophthalmic liquid delivery contact lens 100 in accordance with an embodiment. Contact lens includes a transparent optical zone and an annual periphery 152 outside of the optical zone, therapeutic liquid storage reservoir 154 within periphery 152 of contact lens body 150, channel inlet 124 from reservoir 154 within the periphery to outlet 125 for dispensing liquid to an eye, and flow regulating portion 104 connected with the channel. An eye contact surface is underneath, on the concave side of the contact lens.

Flow regulating portion 104 includes bead traps 110 and 120. Port 108 can be punctured with an injection needle to add or remove beads from bead trap 110. Port 118 can be used for adding and removing beads from bead trap 120. Downstream port 128 may be used by a second injection needle to suck or push fluid such that microscopic beads within bead traps 110 and 120 are moved into or out of the bead traps.

In this embodiment, therapeutic reservoir 154 may be actuated by a finger press to apply a mechanical force to actuate the therapeutic. Such a manual press area is on an outer surface of periphery 152 of the contact lens over a portion of the therapeutic reservoir. The manual press area is configured to apply pressure to the therapeutic reservoir when the area is pressed.

The therapeutic liquid storage reservoir may be actuated by the closing and opening of the wearer's eyelids. As the eyelid closes, it increases pressure on therapeutic liquid storage reservoir 154, thereby increasing the internal pressure and actuating the drug. When the eyelid opens, the reservoir returns to a normal shape. This may create a vacuum which may draw fluid back into the reservoir. A one-way check valve in the fluidic path could prevent such fluid draw back.

The device may further include an actuation chamber interacting with the therapeutic reservoir to actuate the therapeutic delivery without external forces (e.g. finger pressing on therapeutic reservoir). The contact lens can include an actuation chamber, and a flexible diaphragm between the actuation chamber and the reservoir.

The contact lens can also include a reservoir fill port connected with the storage reservoir for refilling the contact lens reservoir with a therapeutic fluid. The reservoir fill port can include an elastomer that is configured to self seal after a piercing needle is withdrawn therefrom.

The fill port may be situated with a needle stop surface on the side opposite the resealing elastomer. The needle stop may consist of a thickened portion of the contact lens or a denser pierce resistant material. Preferably a non-coring needle, non-piercing needle, side port needle, or needle with a combination of the above mentioned features is used to prevent damage to the needle stop surface.

The contact lens may include microchannels on the surface that interfaces with the eye. Such microchannels will preferably wick the therapeutic liquid from the exit port, thereby providing an even layer of therapeutic liquid throughout the contact layer surface, thereby improving efficacious surface area. Alternatively, the microchannels may preferably direct therapeutic fluid to specific regions while preventing or guiding liquid away from other regions.

The contact lens may be an ophthalmic eye hydration contact lens. The eye hydration contact lens can include a sponge material disposed in an annulus and a water-impermeable shell substantially covering the outer convex surface of the sponge material annulus. The annular sponge material is curved axially to form an inner concave surface and an outer convex surface and includes water-absorbing pores. The actuation chamber can also include a semi-permeable membrane that divides the actuation chamber into an osmotic chamber and a fluid chamber. Fluid from the fluid chamber is able to permeate the semi-permeable membrane into the osmotic chamber and increase the pressure within the osmotic chamber to deflect a portion of the diaphragm into the reservoir. A difference in solute concentration, the solutes being impermeable to the semi-permeable membrane, between the osmotic chamber and the fluid chamber provides the driving force for the fluid from the fluid chamber permeating the semi-permeable membrane.

In various embodiments, the transparent optical zone of the contact lens may be an aperture. Such an embodiment benefits from the fit and functionality of a regular contact lens but does not require the optical zone to contain any material, thereby allowing for intuitive application and removal for users.

The aperture size may be greater than the optical zone and can be at least 1, 2, 3, 4, 5, 6, 7, 8, 9, 10 or more millimeters in diameter. Ideally the aperture is 10 mm or greater, thereby being outside of the optical zone of a human patient, even when the pupils are fully dilated. In other embodiments, the aperture may be 12 mm, 14 mm, or 16 mm to avoid interaction with the patient's line of sight even if the contact lens shifts.

In various embodiments, the contact lens may be worn alongside a vision correction contact lens. The therapeutic contact lens may be placed first or after the vision correction contact lens. The therapeutic contact lens may consist of a gradient curvature to allow the vision correction contact lens to co-centrally align, thereby providing reduced mechanical impedance.

The fluidic channel may include two or more outlets to control fluid outflow rate to a plurality of target regions. The device may benefit from having multiple outlets along the outer perimeter, the inner portion, and the inner perimeter (in case of an aperture near the optic zone) to treat various diseases. The distance and order from the actuation mechanism, outlet size, and number of outlets may dictate the fluid flow to each target region.

The contact lens can further contain an indicator portion. The indicator portion is visible through the optical zone where the patient may see a color change in their iris. Alternatively, and preferably, the indicator portion would be in the sclera, or white outer layer where a color change is more visible against the white backdrop compared to the iris. The indicator portion alerts the user that the medication is exhausted, level of medication is low, or the drug delivery rate is low. The indicator may be implemented by a chemical interaction with the drug, an optical interaction by the flow or presence of drug. The indicator portion is a portion of the drug delivery channel that interacts with the drug. Thereby, the presence of the drug would maintain the indicator portion as one color, whereas the lack of the drug would change the indicator portion to a different color. The positive drug presence color may be clear, but may beneficially indicate a positively filled or working contact lens by a presence of a color such as green. The negative drug presence color may be a lighter color showing a waning of the therapeutic level, clear showing empty, or an obvious color change such as red.

Figure 2A:
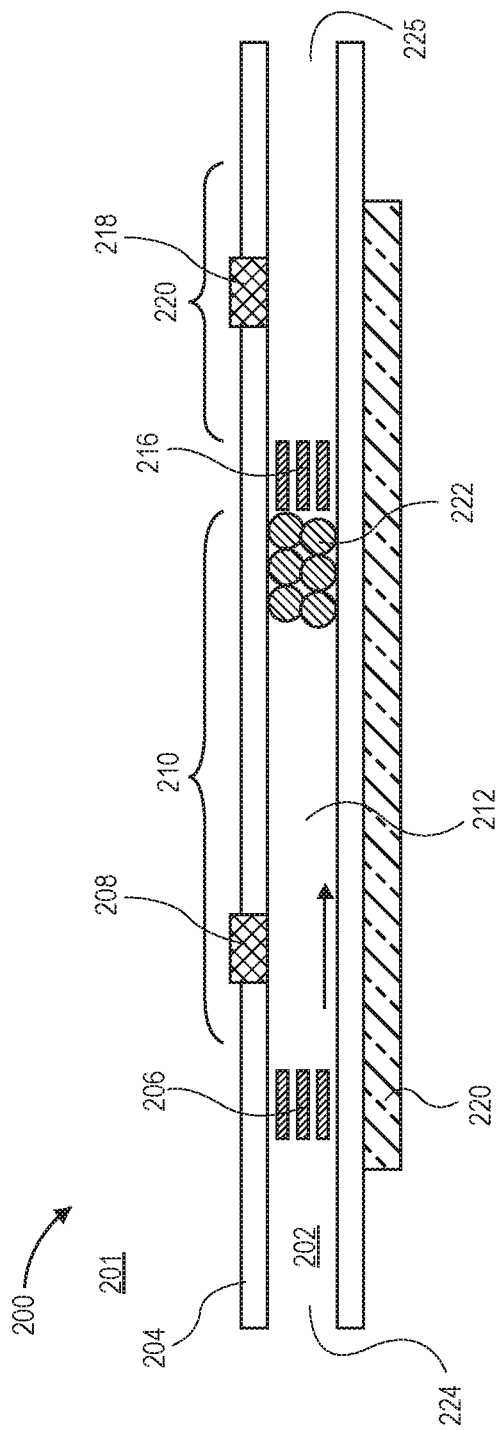
FIG. 2A is a side view of a flow restrictor having a single bead trap in accordance with an embodiment.
Figure 2B:
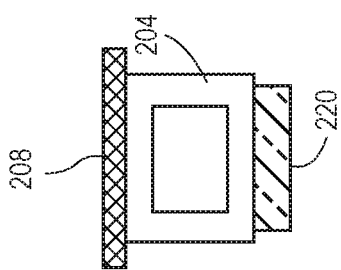
FIG. 2B is an end view of the flow restrictor of FIG. 2A.

FIGS. 2A-2B illustrate a flow restrictor 200 having a single bead trap in accordance with an embodiment.

Flow restrictor 200 includes fluid channel 212 having walls 204. Fluid can enter through inlet 224 and exit through outlet 225. In the figure, bead stop 206 is upstream, while bead stop 216 is downstream such that fluid would flow left to right.

The bead stops may be comprised of one or any combination of the following features: narrow vertical gap(s), narrow horizontal gap(s), narrowing of the channel itself, or a fixed porous material, such as hydrogel, or a filter. In the exemplary embodiment, the bead traps are shown as a filter with narrow gaps. The criteria for an appropriate bead stop is that the bead sizes cannot pass through it and the overall flow resistance with zero beads should be less than the minimum flow resistance that is anticipated to be necessary.

Bead stops 206 and 216 form a region between them in fluid channel 212 called a "bead trap." Bead trap 210 holds tiny, chemically inert spherical beads 222. Beads 222 purposely restrict the flow through fluid channel 212. Unlike in high-performance liquid chromatography (HPLC), the beads are not meant to chemically interact with the liquid. Also unlike HPLC, the beads intentionally lessen the flow rate of the fluid channel. In some embodiments, the bead trap is less than 1 centimeter long so that it can fit in tiny spaces, such as on a contact lens or in an implantable.

In certain embodiments, porous beads can be used instead of nonporous beads. The porosity of the beads is another variable which may be employed to adjust the flow resistance Fill port 208 allows beads to be filled into bead trap 210. The fill port extends from outside 201 of the flow restrictor 200 to inside 202 of the flow restrictor. Similarly, downstream port 218 extends from outside 201 to inside 202 where the fluid channel is. However, downstream port extends into region 220 that is downstream of bead trap 210.

In some embodiments, fill port 208 is puncturable by an injection needle and prevented from puncturing the other side by non-pierceable needle stop on wall 204 opposite fill port 208. Similarly, downstream port 218 is puncturable by an injection needle and backed by the same non-pierceable needle stop 220.

A "non-pierceable" needle stop includes those made out of glass or other hard material that does not allow a standard injection needle to puncture it under customary and usual forces in normal clinical operation, or as otherwise known in the art.

Ports 208 and 218 are self-sealing ports, being constructed of either silicone rubber having a thickness greater than 160 µm, or parylene C having a thickness greater than 5 µm so as to make them self-sealing to a 21-gauge injection needle. The thicknesses of the ports may or may not be more than the thickness of walls 204 of the fluid channel.

In order to contrast with other portions of the flow restrictor and be more readily seen to a surgeon, the ports may be dyed a color. The fill port may be dyed one color while the downstream port may be dyed a different color.

FIG. 2B is an end view of the flow restrictor of FIG. 2A. Because flow restrictor 200 was created by lithography techniques, building up and etching layers from two-dimensional masks, features such as the bead stops, fill port 208, and walls 204, have squared off corners. This is in contrast to HPLC tubes which often have circular cross sections and other rounded features.

FIGS. 3A-3D illustrate a flow restrictor having beads various upstream, central, or downstream bead traps. Flow restrictor 300 includes inlet 324 to a fluid channel defined by walls 304.

Bead stops 306 and 316 define bead trap 310. Bead stops 316 and 326 define bead trap 320, and bead stops 326 and 336 define bead trap 330. Each of the bead traps has a different length. The lengths of the bead traps may be predetermined to provide a certain flow resistance when filled with beads.

These multiple regions of different sizes may be used to store beads for automatic volume control of the implanted beads, individually and/or any combination. Four versions are shown showing example use of different fixed sizes for the bead traps. (FIG. 3A shows long trap, FIG. 3B shows medium, and FIG. 3C is small. FIG. 3D is combination of two.)

Resistance to flow may be adjusted by using different sized beads. Spherical beads having a common, nominal diameter selected from a value between 10 μm and 100 μm are envisioned for primary uses, although other diameters may be used. In some embodiments, porous gel may be used instead of beads.

Fill port 308 services bead trap 310, while fill ports 318 and 328 service bead traps 320 and 330, respectively. That is, the fill ports may be used to inject beads into, or aspirate beads out of, their respective bead traps.

Downstream port 338 may be used to push or suck liquid in order to dislodge or set the beads into position within the bead traps. Upstream bead trap 305 may be used similarly.

FIG. 3A shows beads filling long bead trap 310, and FIG. 3B shows beads filling medium bead trap 320. FIG. 3C shows beads filling short bead trap 330. FIG. 3D shows beads filling two bead traps, 310 and 330, which are the long and short bead traps.

Figure 4:
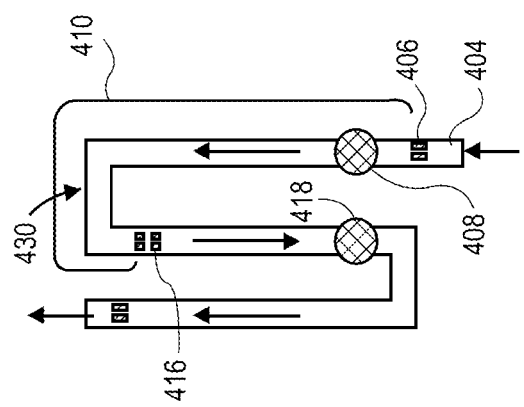
FIG. 4 illustrates a U-shaped flow restrictor in accordance with an embodiment.

FIG. 4 illustrates a flow restrictor with U-shaped section 430. Walls 404 and bead stops 406 and 416 define bead trap 410. Fill port 408 can be used to access bead trap 410. Because of the U shape, downstream port 418 is adjacent fill port 408. This may aid a surgeon in practically handling two injection needles, piercing the adjacent ports.

Figure 5:
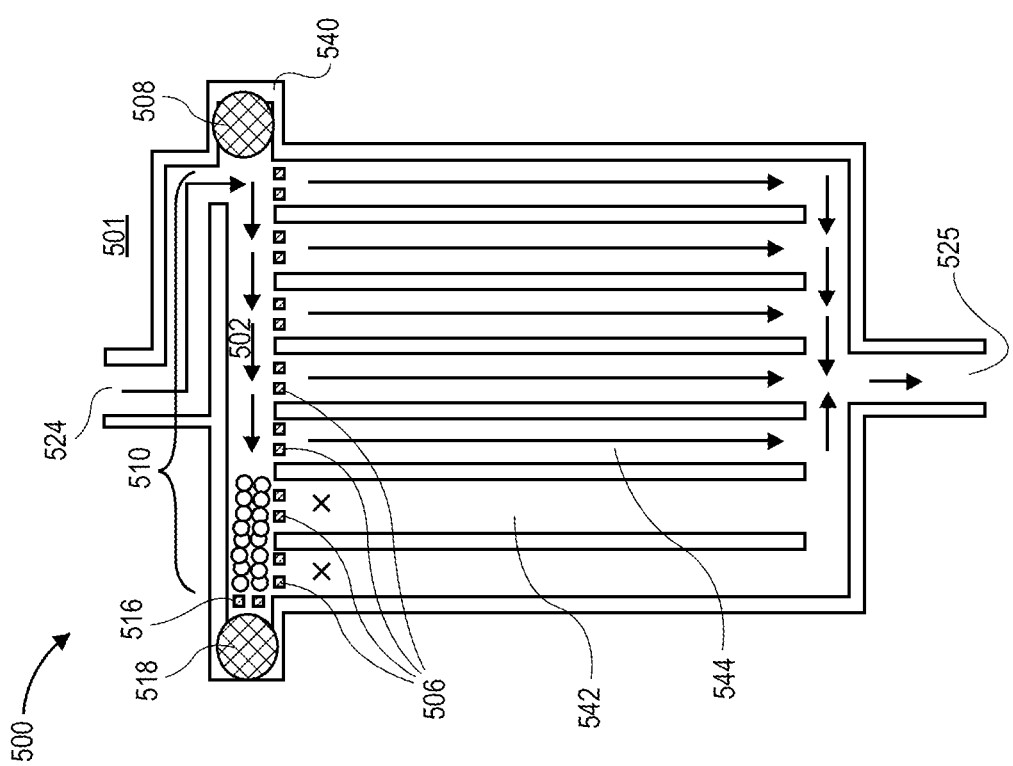
FIG. 5 illustrates a multi-channel flow restrictor in accordance with an embodiment.

FIG. 5 illustrates multi-channel flow restrictor 500, which has inlet 524 feeding into inside of fluid channel 502 of manifold 540. Manifold 540 runs perpendicular to multiple parallel fluid channels, including fluid channels 542 and 544. The fluid channels exit at common outlet 525. At the inlet of each fluid channel is bead stop 506.

Along with bead stops 506, bead stop 516 defines bead trap 510 in manifold 540. Fill port 508 is within bead trap 510 and allows for beads to be added or removed. Downstream port 518 is outside of bead trap 510 and, in the figure, just beyond bead stop 516. It is used to push or pull fluid for moving beads, similarly to the downstream ports in other embodiments. Either or both the fill port and downstream port may be self-sealing.

A flow inhibitor such as beads, viscous gel, hydrogel, can be introduced into fill port 508 in order to close off the desired number of channels such that the flow resistance is determined by the number of open channels. In the exemplary embodiment of the figure, beads block two channels (i.e., fluid channels 542 and 544), leaving the remaining five fluid channels open for flow.

As beads or gel are inserted into fill port 508, suction is applied from downstream port 518 to pull the flow inhibiting material to the left side. Bead stops, filters, or gel stops can be used to contain the flow restricting material to the entrance, fan-out area. The flow resistance through the beads or inhibiting material is much greater than the resistance through each vertical tube such that the flow is approximately controlled by the number of unblocked channels, such that the fluidic resistance of the inhibiting material may be neglected.

Figure 6A:
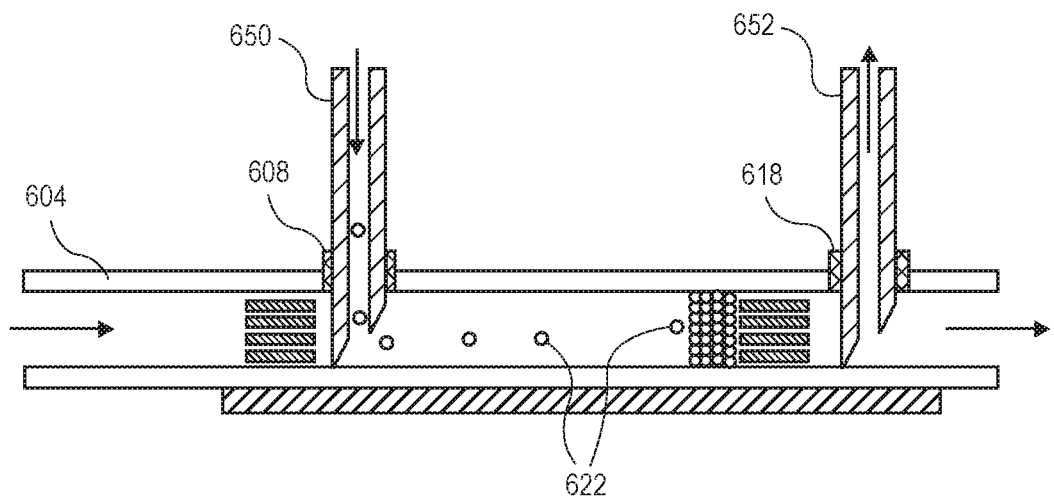
FIG. 6A illustrates the insertion of blocking material into a flow restrictor in accordance with an embodiment.
Figure 6B:
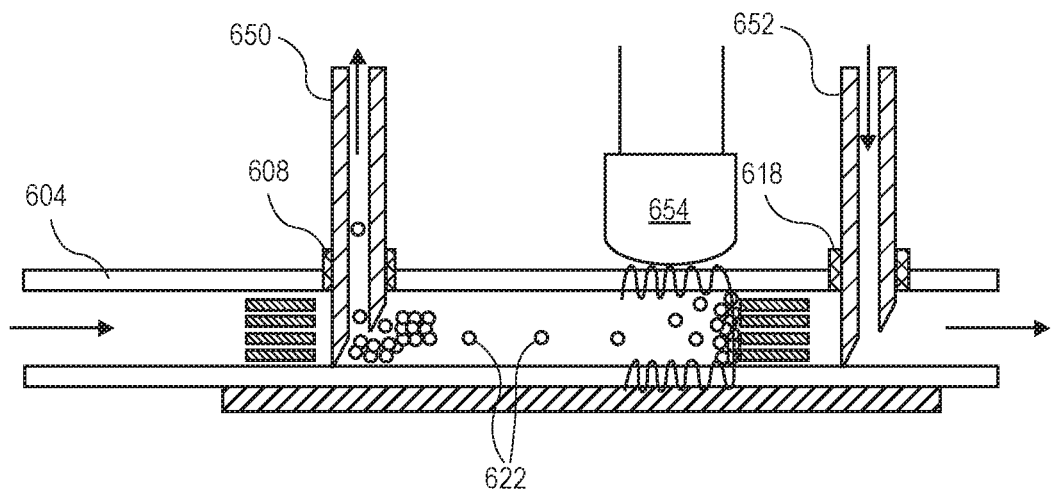
FIG. 6B illustrates the removal of blocking material from a flow restrictor in accordance with an embodiment.

To increase flow, the inhibiting material can be flushed out of fill port 508, and less material can be introduced such that fewer channels are blocked. This will allow a fixed number of optional flow resistances. The flow channels may have different or identical flow resistances, allowing for greater design space for available flow resistance settings FIGS. 6A-6B illustrate needle insertion or removal of blocking material into a flow restrictor in accordance with an embodiment. Fill port 608 is set into flow restrictor wall 604 within a bead trap. Downstream port 618 is set into flow restrictor wall 604 downstream of the bead trap.

Injection needle 650 punctures fill port 608, and injection needle 652 punctures downstream port 618.

Blocking material is injected and removed by dual syringes in opposing push/pull or pull/push arrangements.

In FIG. 6A, drainage is naturally flowing left to right. Injection needle 650 pushes beads 622 into to the bead trap contemporaneously with injection needle 652 sucking fluid. Because needle 652 is in the downstream port beyond the bead stop of the bead trap, no beads are sucked into it.

In FIG. 6B, material is removed by inverting the direction of flow through the needles, such that suction is drawn through the upstream port 608, and liquid is pushed into the downstream port 618. The higher velocity of flow through the needles helps dislodge the blocking material. In this arrangement, the flow through the inlet and outlet is not disturbed by the injection of liquid, but only the flow resistance along the channel.

Ultrasound or vibration can be applied through wall 604 by an ultrasound transducer 654 to dislodge the beads 622 to aid removal. It can also be used in settling and packing the beads during insertion (as in FIG. 6A).

To change the flow resistance, the flow blocking material is removed as in FIG. 6B, and then a different amount of blocking material is inserted as in FIG. 6A. This allows adjustment even after implantation.

Figure 7:
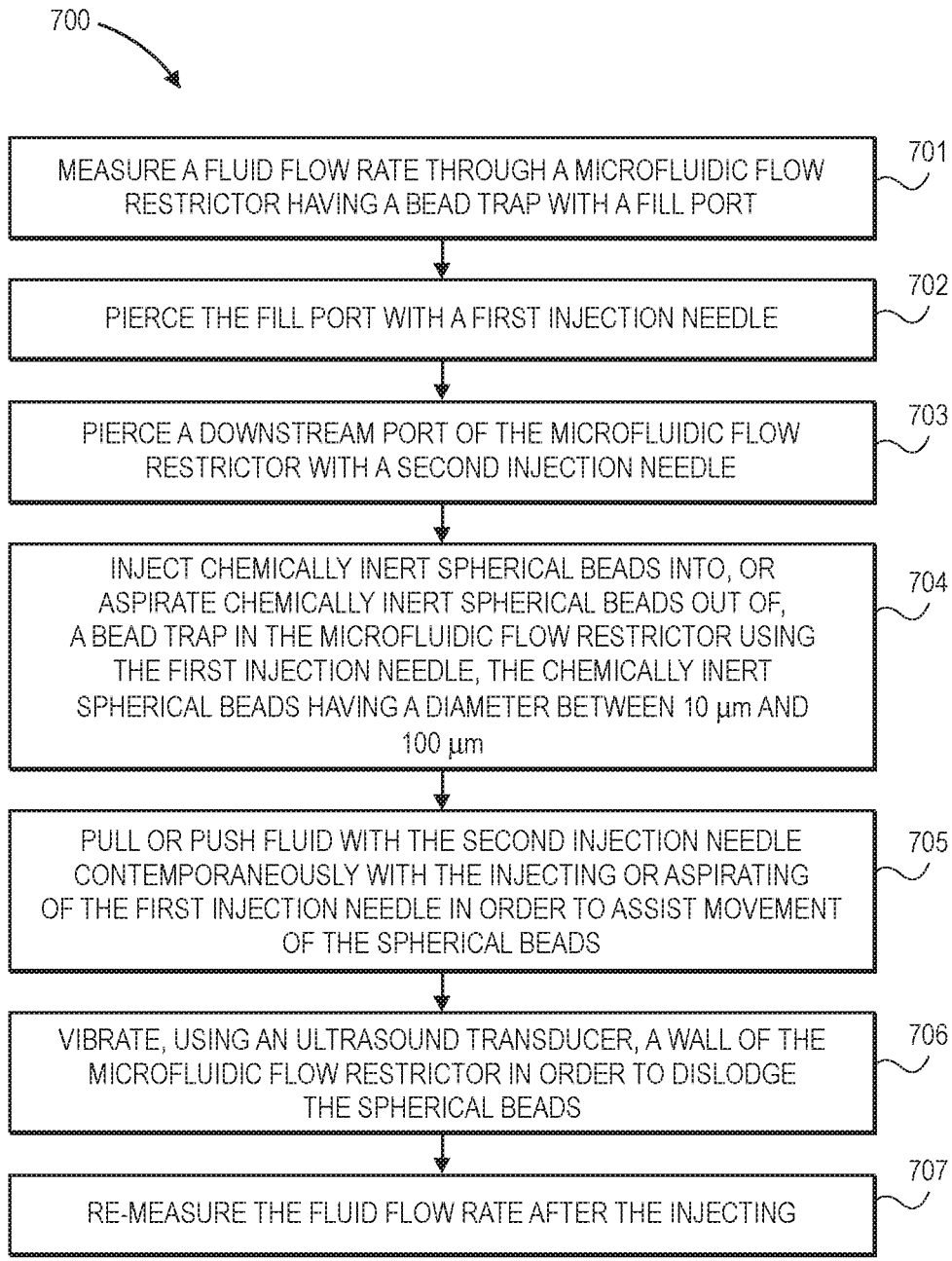
FIG. 7 is a flowchart illustrating a process in accordance with an embodiment.

FIG. 7 is a flowchart illustrating a process in accordance with an embodiment. In operation 701, a fluid flow rate through a microfluidic flow restrictor having a bead trap with a fill port is measured. In operation 702, the fill port is pierced with a first injection needle. In operation 703, a downstream port of the microfluidic flow restrictor is pierced with a second injection needle. In operation 704, chemically inert spherical beads are injected into, or chemically inert spherical beads are aspirated out of, a bead trap in the microfluidic flow restrictor using the first injection needle, the chemically inert spherical beads having a diameter between 10 μm and 100 μm. In operation 705, the second injection needle pulls or pushes fluid contemporaneously with the injecting or aspirating of the first injection needle in order to assist with movement of the spherical beads. In operation 706, an ultrasound transducer vibrates a wall of the microfluidic flow restrictor in order to dislodge the spherical beads. In operation 707, the fluid flow rate is re-measured after the injecting.

The invention has been described with reference to various specific and illustrative embodiments. However, it should be understood that many variations and modifications may be made while remaining within the spirit and scope of the following claims.

What is claimed is:

1. A microfluidic flow restrictor apparatus comprising:
 a fluid channel having walls, a fluid inlet, and a fluid outlet;
 a first bead stop within the fluid channel;
 a second bead stop within the fluid channel, the first and second bead stops forming a bead trap within the fluid channel;
 a fill port extending from an outside of the walls to an interior of the bead trap; and
 a needle port extending from the outside of the walls to a portion of the fluid channel downstream of the bead trap,
 wherein the bead trap forms a U shape such that the fill port is proximate the needle port.

2. The apparatus of claim 1 further comprising:
 a non-pierceable needle stop on or within a wall opposite at least one of the fill port and the needle port.

3. The apparatus of claim 1 further comprising:
 a plurality of chemically inert spherical beads within the bead trap.

4. The apparatus of claim 3 wherein the spherical beads each have a diameter between 10 μm and 100 μm.

5. The apparatus of claim 3 wherein the spherical beads are porous.

6. The apparatus of claim 1 wherein the bead trap is a first bead trap and the fill port is a first fill port, the apparatus further comprising:
 a third bead stop within the fluid channel, the second and third bead stops forming a second bead trap within the fluid channel; and
 a second fill port extending from the outside of the walls to an interior of the second bead trap,
 whereby both or either the first or second bead trap are configured to be selectively filled with beads in order to modify a flow resistance of the microfluidic flow restrictor apparatus.

7. The apparatus of claim 6 wherein the first bead trap has a different length from the second bead trap.

8. The apparatus of claim 6 further comprising:
 a non-pierceable needle stop on or within a wall opposite the second fill port.

9. The apparatus of claim 1 wherein at least one of the fill port or the needle port is thicker than the walls of the fluid channel.

10. The apparatus of claim 9 wherein the fill port and the needle port each comprises silicone rubber and has a thickness greater than 160 μm so as to make them self-sealing to a 21-gauge injection needle.

11. The apparatus of claim 9 wherein the fill port and the needle port each comprises parylene C and has a thickness greater than 5 μm so as to make them self-sealing to a 21-gauge injection needle.

12. The apparatus of claim 1 wherein the fluid channel, first and second bead stops, and fill port have squared off corners resulting from photolithography and etching.

13. A contact lens comprising:
 the microfluidic flow restrictor apparatus of claim 1;
 a reservoir connected with an inlet of the flow restrictor apparatus; and
 an eye-contacting surface connected with an outlet from the microfluidic flow restrictor apparatus.

14. A microfluidic flow restrictor apparatus comprising:
 a fluid channel having walls, a fluid inlet, and a fluid outlet;
 a first bead stop within the fluid channel;
 a second bead stop within the fluid channel, the first and second bead stops forming a first bead trap within the fluid channel;
 a first fill port extending from an outside of the walls to an interior of the first bead trap;
 a needle port extending from the outside of the walls to a portion of the fluid channel downstream of the first bead trap;
 a third bead stop within the fluid channel, the second and third bead stops forming a second bead trap within the fluid channel; wherein the second bead trap has a different length than the first bead trap; and
 a second fill port extending from the outside of the walls to an interior of the second bead trap,
 whereby both or either the first or the second bead trap are configured to be selectively filled with beads in order to modify a flow resistance of the microfluidic flow restrictor apparatus.

15. The apparatus of claim 14 further comprising:
 a non-pierceable needle stop on or within a wall opposite at least one of the first fill port, the second fill port, and the needle port.

16. The apparatus of claim 14 wherein at least one of the first fill port, the second fill port, or the needle port is thicker than the walls of the fluid channel.

17. The apparatus of claim 16 wherein the first fill port and the needle port each comprises silicone rubber and has a thickness greater than 160 μm so as to make them self-sealing to a 21-gauge injection needle.

18. The apparatus of claim 16 wherein the first fill port and the needle port each comprises parylene C and has a thickness greater than 5 μm so as to make them self-sealing to a 21-gauge injection needle.

19. The apparatus of claim 14 wherein the fluid channel, first and second bead stops, and fill port have squared off corners resulting from photolithography and etching.

20. A contact lens comprising:
 the microfluidic flow restrictor apparatus of claim 14;
 a reservoir connected with an inlet of the flow restrictor apparatus; and
 an eye-contacting surface connected with an outlet from the microfluidic flow restrictor apparatus.

\* \* \* \* \*